(12) United States Patent
Letard et al.

(10) Patent No.: US 8,963,106 B2
(45) Date of Patent: Feb. 24, 2015

(54) METHOD FOR THE THERMAL PHOTOSWITCHING OF SPIN-TRANSITION MATERIALS, AND USES THEREOF

(75) Inventors: Jean-Francois Letard, Canejan (FR); Eric Freysz, Pessac (FR)

(73) Assignee: Centre National de la Recherche Scientifique, Paris (FR)

( * ) Notice: Subject to any disclaimer, the term of this patent is extended or adjusted under 35 U.S.C. 154(b) by 105 days.

(21) Appl. No.: 13/811,006

(22) PCT Filed: Jul. 20, 2011

(86) PCT No.: PCT/FR2011/051750
§ 371 (c)(1),
(2), (4) Date: Apr. 2, 2013

(87) PCT Pub. No.: WO2012/010801
PCT Pub. Date: Jan. 26, 2012

(65) Prior Publication Data
US 2013/0214179 A1 Aug. 22, 2013

(30) Foreign Application Priority Data
Jul. 22, 2010 (FR) ...................................... 10 55975

(51) Int. Cl.
G01N 21/00 (2006.01)
C07F 15/02 (2006.01)
G11B 7/248 (2006.01)
B41M 5/26 (2006.01)
G11B 7/2492 (2013.01)
H01L 29/66 (2006.01)
C07D 249/08 (2006.01)

(52) U.S. Cl.
CPC ......... *H01L 29/66984* (2013.01); *B41M 5/262* (2013.01); *B41M 5/267* (2013.01); *G11B 7/2492* (2013.01); *B41M 5/26* (2013.01); *C07D 249/08* (2013.01)
USPC ................. 250/492.1; 250/495.1; 250/504 R; 540/3; 548/101; 548/269.2

(58) Field of Classification Search
USPC .................... 250/492.1, 495.1, 504 R; 540/3; 548/101, 269.2
See application file for complete search history.

(56) References Cited

U.S. PATENT DOCUMENTS 8,709,599 B2 * 4/2014 Letard et al. ................... 428/402
2008/0311401 A1 * 12/2008 Letard et al. ................... 428/404

FOREIGN PATENT DOCUMENTS

| FR | 2755696 | 5/1998 |
| FR | 2917410 | 12/2008 |
| WO | 2007065996 | 6/2007 |

OTHER PUBLICATIONS

International Search Report dated Oct. 19, 2011.
Room temperature study of the optical switching of a spin crossover compound inside its thermal hysteresis loop dated Jan. 27, 2010.

* cited by examiner

*Primary Examiner* — Nikita Wells
(74) *Attorney, Agent, or Firm* — Sofer & Haroun, LLP

(57) ABSTRACT

A method is provided for the thermal photoswitching of spin-transition compounds from the low-spin state to the high-spin state, including at least one step of exposing the material to a non-polarized laser beam which is at room temperature, and the wavelength of which is in the infrared range and the power of which is 1 mW·cm$^{-2}$ to 1 W·cm$^{-2}$. The method may be used for the temporary or permanent marking of materials including particles of at least one spin-transition compound including an iron(II) and triazole ligand compound.

13 Claims, 2 Drawing Sheets

METHOD FOR THE THERMAL PHOTOSWITCHING OF SPIN-TRANSITION MATERIALS, AND USES THEREOF

RELATED APPLICATIONS

This application is a National Phase Application of PCT/FR2011/051750, filed on Jul. 20, 2011, which in turn claims the benefit of priority from French Patent Application No. 10 55975 filed on Jul. 22, 2010, the entirety of which are incorporated herein by reference.

BACKGROUND

1. Field of the Invention

The present invention relates to a process for the thermal photoswitching of spin-transition compounds and to the use of such a process in the temporary or permanent marking of materials comprising particles of at least one spin-transition compound.

2. Description of Related Art

Compounds involving the iron(II) ion based on a triazole ligand, and the materials incorporating them, are known to exhibit the phenomenon of spin transition, combining a memory effect (thermal hysteresis in the vicinity of ambient temperature) with a modification to the optical (changing color), magnetic and structural properties. These properties are taken advantage of in use of its materials in various applications, in particular in information storage. Such compounds can be coordination complexes comprising one or more metal centers having a $3d^4$, $3d^6$ or $3d^7$ configuration, one or more nitrogenous ligands and one or more anions, such as described, for example, in patent applications EP-0 543 465, EP-0 666 561, EP-0 745 986 and EP-0 842 988, international application WO2007/065996 and patent application FR 2 917 410.

By way of example, patent application EP-0 543 465 describes iron-based spin-transition compounds and their use in information storage. Some of these compounds correspond to one of the following formulae:

$FeL_3(NO_3)_2$ in which L is a ligand of the 1,2,4-triazole or 4-amino-1,2,4-triazole type combined with the $NO_3^-$ anion;

$Fe(ATP)_2 \cdot 5Cl_2$, in which the ATP ligand is 4-amino-1,2,4-triazole combined with Fe(II) and with $Cl^-$;

$Fe(TP)_2Cl_2$, in which the TP ligand is 1,2,4-triazole, combined with $Cl^-$;

[Fe(2-aminomethylpyridine)$_3$]Cl$_2$·EtOH, EtOH being ethanol;

[Fe(1,10-phenanthroline)$_2$](NCS)$_2$;

[Fe(1-propyltetrazole)$_6$](BF$_4$)$_2$.

With the exception of [Fe(1,10-phenanthroline)$_2$(NCS)$_2$], these compounds are pink in the low spin (LS) state and white in the high spin (HS) state.

International application WO2007/065996 describes a material in the form of complex nanoparticles corresponding to the following formula (I):

$$[(Fe_{1-y}M_yL_3)_wL_3][X'_{2/x(1-z/x')}Y'_{2z/x'}]_w \quad (I)$$

in which:

L represents a 1,2,4-triazole ligand carrying an R substituent on the nitrogen in the 4 position;
X' is an anion having the valency x, $1 \leq x \leq 2$;
Y' is an anion other than X having the valency x', $1 \leq x' \leq 2$;

R is an alkyl group or an $R^1R^2N-$ group in which $R^1$ and $R^2$ each represent, independently of the other, H or an alkyl radical;
M is a metal having a $3d^4$, $3d^5$, $3d^6$ or $3d^7$ configuration, other than Fe;
$0 \leq y \leq 1$, $0 \leq z \leq 2$ and $3 \leq w \leq 1500$.

The compounds described in this document are pink in the LS state and white in the HS state.

Patent application FR 2 917 410 describes a spin-transition material composed of at least one compound corresponding to the following formula (II):

$$AX_bY_c \quad (II)$$

in which:

A corresponds to the formula $Fe_{1-m}M_m(R-Trz)_3$;
M is a metal having a $3d^4$, $3d^5$, $3d^6$ or $3d^7$ configuration, other than Fe;
$0 \leq m \leq 1$;
R-Trz represents a 1,2,4-triazole ligand carrying an R substituent on the nitrogen in the 4 position;
R is an alkyl group or an $R^1R^2N-$ group in which $R^1$ and $R^2$ each represent, independently of the other, H or an alkyl radical;
X represents at least one monovalent or divalent anion;
Y represents at least one anion which has a chromophore group;
b and c are chosen so that the electrical neutrality of the compound (II) is respected. The color of each spin state of this material can be adjusted by appropriately choosing the X and Y anion or anions and by controlling their respective proportions in the material.

The document FR 2 755 696 describes a spin-transition compound including a network comprising molecules each formed of a metal-ligand complex and of an anion, in which the metal is composed of at least one metal ion having a $d^4$, $d^5$, $d^6$ or $d^7$ electronic configuration, in which the ligand comprises at least one aminotriazole group or a substituted aminotriazole group, and in which the anion is formed of an alloy of at least two anions including an anion having a nitrate ($NO_3^-$) radical. This document also describes a data display device comprising a system forming a screen and a thermal addressing system. This thermal addressing system comprises heating means B1 (such as a laser beam with a wavelength in the infrared region). The function of the laser beam is thus not to switch the abovementioned compound but to monitor the photoswitching phenomenon.

Several methods which make it possible to bring about the spin transition of these compounds, that is to say which make it possible to change these compounds from an LS state to an HS state, have already been provided.

According to EP-0 543 465 and FR 2 917 419, the spin transition is brought about by heating or cooling and takes place between −20° C. and +100° C. The hysteresis phenomenon can range from a few degrees to a few tens of degrees, according to the compounds.

Some authors, such as Freysz et al. (Chemical Physics Letters, 2004, 394, 318-323), provide for the application of laser radiation at the center of the thermal hysteresis loop of iron-based spin-transition materials ([Fe(PM-BiA)$_2$(NCS)$_2$] complex with PM-BiA=N-(2'-pyridylmethylene)-4-aminobiphenyl), in order to bring about photoconversion from the LS state to the HS state. According to this document, irradiation is carried out for a few minutes at a wavelength of 830 nm (near infrared), at a power of 5 mW·cm$^{-2}$ and at a temperature of 10 K (i.e., approximately −263.15° C.). Above a tempera ture of −100° C., photoswitching according to this process is no longer observed.

Other authors, such as Bonhommeau S. et al. (Angew. Chem. Int., 2005, 44, 4069), report a single laser irradiation test on a spin-transition material of [Fe(pyrazine){Pt(CN)$_4$}] type in the dehydrated state. According to this document, irradiation is carried out in the visible region at a wavelength of 532 nm with pulses having a duration of 8 ns. However, there are a number of disadvantages to this technique. It requires the use of a nanosecond laser pulse having an energy of several tens of millijoules. In addition the central wavelength of the pulse has to be within the absorption range of the material.

These various laser irradiation methods used to date are based on the LIESST (Light-Induced Excited Spin State Trapping) effect, which is an electron photoexcitation of the metal ions, such as the iron ions, of the spin-transition complexes.

The major disadvantage of these methods is that they have to be carried out at extremely low temperatures (of the order of approximately −260° C.) and that they do not make possible the photoswitching of the spin-transition compounds when they are applied at ambient temperature, which is a major limitation on the application of these processes in industry.

The scientific publication by Gallé et al. ("Room temperature study of the optical switching of a spin crossover compound inside its thermal hysteresis loop", Applied Physics Letters, AIP, AMERICAN INSTITUTE OF PHYSICS, vol. 96, No. 4, of Jan. 27, 2010, pages 41907-1 to 41907-3) describes a process for the photoswitching of a spin-transition material from the low spin state to the high spin state comprising a stage of exposure of said material to pulsed laser radiation at a wavelength of between 0.355 µm and 0.532 µm, at ambient temperature and at a power of 52 mJ·cm$^{-2}$ for 6 ns, i.e. $8.66 \times 10^{+6}$ W/cm$^{-2}$. However, this process exhibits the disadvantage of requiring considerable power and of consequently being expensive to carry out.

OBJECTS AND SUMMARY

The inventors thus set themselves the aim of developing a process which can be carried out efficiently at ambient temperature in order to change spin-transition compounds from an LS state to an HS state.

The inventors have now found that, surprisingly, the application of laser radiation with a wavelength within the infrared range makes it possible, under certain conditions, to switch spin-transition materials from an LS state to an HS state.

A first subject matter of the present invention is thus a process for the photoswitching of a spin-transition material from the low spin state to the high spin state comprising a compound based on iron(II) and on a triazole ligand, characterized in that it comprises at least one stage of exposure of said material to unpolarized laser radiation at a wavelength within the infrared range, at ambient temperature and at a power of from 1 mW·cm$^{-2}$ to 1 W·cm$^{-2}$.

This is because the inventors have established that, when a spin-transition material comprising a compound based on iron(II) and on a triazole ligand is submitted to such conditions at ambient temperature, there is observed a localized increase in the temperature of the photo-irradiated material which brings about its switching from the LS state to the HS state. This phenomenon is completely independent of the LIESST effect and makes it possible to bring about spin transition at ambient temperature, whereas to date this could not be envisaged by applying the methods of the prior art.

The process in accordance with the invention in addition exhibits the following advantages:

it is applicable to all spin-transition compounds comprising a compound based on iron(II) and on a triazole ligand, the powers required in order to cause the materials to optically switch are low and compatible with compact and inexpensive laser microsources, it is suitable for the photoswitching of any type of spin-transition compound comprising a compound based on iron(II) and on a triazole ligand in the liquid or solid state, it makes it possible to photoswitch pure materials and/or materials diluted in various matrices, the photoswitching region can be easily controlled by the size of the focusing of the radiation on the sample, the degree of photoswitching of the compound can be adjusted optically, the sweep rate of the compound which it is desired to photoswitch can be controlled as a function of the wavelength and of the laser power density used, the depth of the sample on which photoswitching is induced can be adjusted: it depends on the laser power used and on the sweep rate, the use of coherent radiation makes it possible to inscribe preprogrammed designs without sweeping the surface of the sample, photoswitching is reversible or irreversible at ambient temperature as a function of the nature of the spin-transition material to which the process is applied, as regards the materials, the photoswitching of which is irreversibly induced, the process results in irreversible optical addressing at ambient temperature, which is particularly advantageous for data storage applications or inscription applications of any type: advertising, marking, drawing, art, decoration, detection, and the like, it makes possible the optical addressing of spin-transition materials comprising a compound based on iron(II) and on a triazole ligand.

According to a preferred embodiment of the process in accordance with the invention, the exposure of said material is carried out at a wavelength varying from 0.78 to 30 µm and more preferably still from 5 to 20 µm approximately.

The laser radiation can be continuous or by pulses.

According to a preferred embodiment, the spin-transition material is subjected to continuous laser radiation.

The power of the laser radiation preferably varies from 80 to 500 mW·cm$^{-2}$, a power of the order of 100 mW·cm$^{-2}$ being very particularly preferred.

The duration of the exposure of the spin-transition material to the laser radiation can vary from a few milliseconds at a power of 100 mW·cm$^{-2}$ to approximately a hundred seconds at a power of 1 mW·cm$^{-2}$.

The size of the laser radiation can vary as a function of the surface of the sample which it is desired to photoswitch and of the application which it is desired to give to the process. Generally, the size of the laser beam can vary from 100 µm in diameter at a power of 100 mW·cm$^{-2}$ to 1 mm at a power of 1 W·cm$^{-2}$.

According to the invention, the laser radiation can be applied both to a spin-transition material in the crude state, that is to say in the form of particles, and to a spin-transition material (STM) incorporated in dispersed form in a solid matrix, for example chosen from plaster, varnishes, cements, paints and polymer matrices (PPMA, PVA, and the like).

The STM particles which can be used according to the process of the invention are preferably nanometric or micrometric in size.

"Nanometric" particles is understood to mean particles which have a mean diameter between 1 nm and 500 nm inclusive, more particularly between 1 and 100 nm inclusive.

"Micrometric" particles is understood to mean particles which have a mean diameter between 1 µm and 500 µm inclusive, and more particularly between 100 and 200 µm inclusive.

The spin-transition materials which can be used according to the process in accordance with the present invention can be chosen from many spin-transition materials comprising a compound based on iron(II) and on a triazole ligand described in the prior art, the spin transition of which is reversible or irreversible at ambient temperature.

Mention may in particular be made of STMs in the form of nanometric particles, such as are described in international application WO2007/065996. Mention may in addition be made of spin-transition materials in the form of nanometric or micrometric particles which exhibit varied colors with a defined spin transition, indeed even, for some of them, at least two spin transition temperatures, such as are described in particular in patent application FR 2 917 410.

The spin-transition materials described in international application WO2007/065996 and denoted hereinafter by "materials (I)" are composed of nanometric particles essentially comprising a compound corresponding to the following formula (I):

$$[(Fe_{1-y}M_yL_3)_wL_3][X'_{2/x(1-z/x')}Y'_{2z/x'}]_w \qquad (I)$$

in which:
  L represents a 1,2,4-triazole ligand carrying an R substituent on the nitrogen in the 4 position;
  X' is an anion having the valency x, $1 \leq x \leq 2$;
  Y' is an anion other than X having the valency x', $1 \leq x' \leq 2$;
  R is an alkyl group or an $R^1R^2N$— group in which $R^1$ and $R^2$ each represent, independently of the other, H or an alkyl radical;
  M is a metal having a $3d^4$, $3d^5$, $3d^6$ or $3d^7$ configuration, other than Fe;
  $0 \leq y \leq 1$, $0 \leq z \leq 2$ and $3 \leq w \leq 1500$.

When w in the formula (I) is respectively 3, 300 or 1500, the mean size of the particles is respectively approximately 1 nm, 100 nm or 500 nm.

The spin-transition materials described in patent application FR 2 917 410, denoted hereinafter by "materials (II)", are composed of at least one compound corresponding to the following formula (II):

$$AX_bY_c \qquad (II)$$

in which:
  A corresponds to the formula $Fe_{1-m}M_m(R\text{-}Trz)_3$;
  M is a metal having a $3d^4$, $3d^5$, $3d^6$ or $3d^7$ configuration, other than Fe;
  $0 \leq m \leq 1$;
  R-Trz represents a 1,2,4-triazole ligand carrying an R substituent on the nitrogen in the 4 position;
  R is an alkyl group or an $R^1R^2N$— group in which $R^1$ and $R^2$ each represent, independently of the other, H or an alkyl radical;
  X represents at least one monovalent or divalent anion;
  Y represents at least one anion which has a chromophore group;
  b and c are chosen so that the electrical neutrality of the compound (II) is respected.

In the continuation of the text, a "1,2,4-triazole ligand carrying an R substituent on the nitrogen in the 4 position" is denoted without distinction by L or by R-Trz.

A material (II) can be composed of a single compound (II) having one or more different coloring anions or of a mixture of at least two compounds which correspond to the definition given above for (II).

In a compound (II), X can represent one or more anions, preferably one or two anions $X^1$ and $X^2$. The anions are chosen from monovalent anions or divalent anions. A monovalent anion can be chosen from $BF_4^-$, $ClO_4^-$, $Br^-$, $Cl^-$, $NO_3^-$, $CF_3SO_3^-$, $CH_3SO_3^-$ and 3-nitrophenylsulfonate. A divalent anion is preferably chosen from $SO_4^{2-}$ and $CO_3^{2-}$. Mention may be made, as examples of mixture of anions, of the pair $BF_4^-$ and $NO_3^-$, the pair $Br^-$ and $NO_3^-$ or the pair $Cl^-$ and $NO_3^-$.

Y represents one or more chromophoric anions, preferably one or two anions $Y^1$ and $Y^2$.

An anion Y is preferably chosen from chromophoric anions which have at least two aromatic rings and at least one $SO_3^-$ group. Such anions are provided in particular by the compounds referred to as "acid dyes" or "direct dyes" or "brilliant dyes" or "mordant dyes".

The anion Y of these dyes can comprise:
  an azo group, such as, for example, C. I. Acid Orange 5, which is the monosodium salt of 4-[[4-(phenylamino)-phenyl]azo]benzenesulfonic acid, or Acid Yellow 23, which is tartrazine, corresponding to the formula:

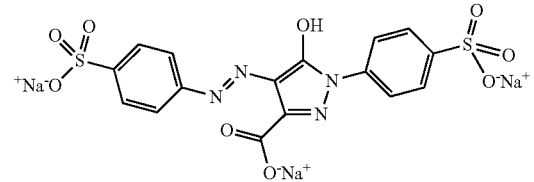

or Methyl Orange or Acid Orange 52 (helianthine) corresponding to the formula:

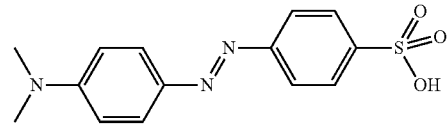 [SMILES: CN(C)c1ccc(/N=N/c2ccc(S(=O)(=O)O)cc2)cc1]

or various Direct Scarlet; or C. I. Direct Blue 1, corresponding to the formula:

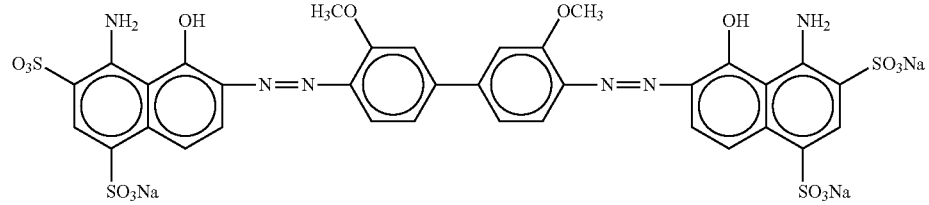

or C.I. Acid Red 27, corresponding to the formula:

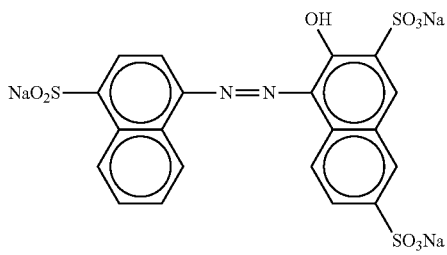

a group derived from an anthraquinone, for example C. I. Reactive Blue 4, corresponding to the formula:

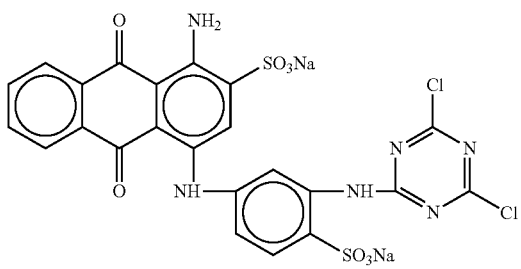

a group derived from a quinoline (C. I. Acid Yellow 3; D&C Yellow No. 30).

In a material (II), the proportions of anions X and Y are such that the electronic neutrality of the compound is respected.

The color of each spin state of a material (II) can be adjusted by appropriately choosing the anion or anions X and Y and by controlling their respective proportions in the material.

It is necessary for the proportion of coloring anion Y to be greater than a certain threshold in order to avoid obtaining a compound exhibiting a pink color in the low spin state and a white color in the high spin state.

It is also necessary for the proportion of coloring anion to be lower than a certain threshold above which the colors corresponding to the low spin state and to the high spin state are difficult to distinguish.

Two conditions are to be observed:
1. a c/b (that is to say, (number of moles of Y)/(number of moles of X) molar ratio: it is less than or equal to 0.1 and greater than or equal to $10^{-5}$;
2. a limiting concentration of Y anion, generally of between $10^{-7}$ and $5 \times 10^{-4}$ mole/L (for example, for Patent Blue, between $4 \times 10^{-7}$ and $2 \times 10^{-4}$ mole/L and, for tartrazine, between $2.2 \times 10^{-7}$ and $1.1 \times 10^{-4}$ mol/L).

Among the STMs of formula (II) above, those in which the R substituent of the 1,2,4-triazole ligand is a hydroxyalkyl radical, such as, for example, a β-hydroxyethyl radical, and X is a 3-nitrophenylsulfonate anion are irreversible STMs, that is to say for which the spin transition from the high spin state to the low spin state is irreversible at ambient temperature after photoswitching according to the process in accordance with the invention. The photoswitching of irreversible STMs is accompanied by a desolvation phenomenon.

In addition, a subject matter of the invention is the use of the process as defined above for the marking of materials comprising particles of at least one spin-transition compound comprising a compound based on iron(II) and on a triazole ligand.

Said marking can be temporary or definitive, as a function of the nature of the spin-transition compound. Thus, when the spin-transition compound is a "reversible" compound, that is to say a compound for which the change to the HS state is reversible at ambient temperature, then the marking can be temporary. On the other hand, when the spin-transition compound is an "irreversible" compound, that is to say a compound which remains in the HS state at ambient temperature, then the marking is permanent.

The process in accordance with the invention thus has applications in any type of industry and in particular can thus be used in the field of information processing, data storage, optical addressing, materials sciences, plastics technology, varnishes, decoration, and the like.

DETAILED DESCRIPTION

The present invention is described in more detail using the following examples, which are given by way of illustration and to which the invention is, of course, not limited.

EXAMPLES

The starting materials and equipment used in the examples which follow are listed below:
[Fe(R-Trz)$_3$NO$_3$], with R=NH$_2$, the preparation of which is described in patent application FR 2 917 410;
[Fe(R-Trz)$_3$X$_2$], with R=—(CH$_2$)$_2$OH and X=3-nitrophenylsulfonate, the preparation of which is described in patent application FR 2 917 410;
Colorless varnish for metals, sold under the trade name Vernis Métaux, le Secret de l'Ebéniste®, by Syntilor;
Gypsum plaster, sold under the trade name Enduit de Rebouchage Poudre Chrono by Toupret;
Polymethyl methacrylate (PMMA) sold under the reference M.W. 38000 Beads by Acros Organics;
White alkyd lacquer paint, sold under the reference Base P, Gamme Prestige, by Tollens;
99% Pure acetonitrile (Aldrich);
CO$_2$ laser, Duo Lase® model, sold by Synrad Inc.

The spin-transition compounds were placed in front of a laser source continuously delivering approximately one hundred milliwatts in the infrared range. The unpolarized radiation emitted by this source was used directly on the material, without specific precaution. In order to register the photoswitching, the sample was placed in front of the laser beam either by hand by the experimenter or by using a micrometer table which makes it possible to control the sweep rate.

Example 1

Photoswitching of a Spin-Transition Compound of the Family of the Iron(II) R-Triazole Compounds In this example, the reversible photoswitching was carried out on the following compound: [Fe(NH$_2$-Trz)$_3$NO$_3$].

The [Fe(NH$_2$-Trz)$_3$NO$_3$] sample, in the form of a powder formed of micrometric grains, was placed under the laser radiation at a power of 150 mW·cm$^{-2}$. The wavelength of the laser was 10.6 µm. The compound was exposed for only a few milliseconds.

Figure 1:
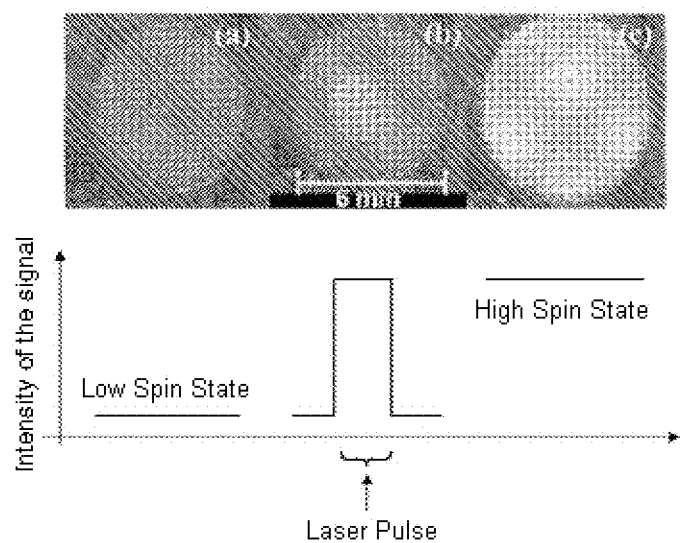
FIGS. 1(a)-1(c) are images of the material of example 1, in accordance with one embodiment.

The appended FIG. 1 is a photograph of the material before irradiation (1a), during laser irradiation (1b) and after irradiation (1c).

After photo-excitation, these compounds, pink in the LS state, become white in the HS state. It is observed that the compound has been completely photoswitched.

Example 2

Photoswitching of a Spin-Transition Compound of the Family of the Iron(II) R-Triazole Compounds Inserted into a Polymer Matrix In this example, the reversible photoswitching of [Fe(NH$_2$-Trz)$_3$NO$_3$] was carried out after having inserted it into a polymer matrix composed of a colorless varnish for metals sold under the trade name Vernis Métaux, le Secret de l'Ebéniste®, by Syntilor, in a proportion of 5% by weight.

The sample was placed on a computer-controlled translation table. An interrupter, this also computer-controlled, made it possible to interrupt the laser illumination of the sample. The sweep rate, adjustable by a computer, was regulated at 1 cm·s$^{-1}$ and the power of the laser was 100 mW·cm$^{-2}$. The diameter of the laser beam was 1 mm. Irradiation was carried out at a wavelength of 10.6 µm.

In this example, letters were inscribed on the sample; each letter was inscribed by a single laser sweep, the laser beam being blocked before the inscription of each of the letters.

Figure 2:
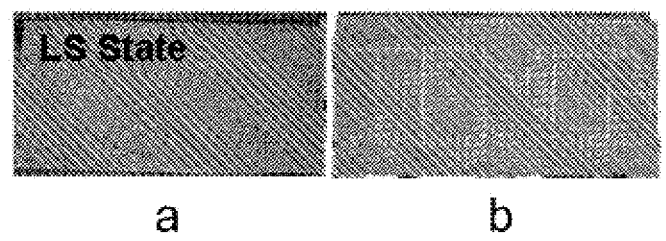
FIGS. 2(a)-2(b) are images of matrix incorporating the transition material of example, 2, in accordance with one embodiment.

The appended FIG. 2 is a photograph of the matrix incorporating the transition material before irradiation (2a) and after irradiation (2b). In this case, the irradiation and the sweeping of the sample were carried out so as to obtain the script "ICMCB" at the surface of the matrix.

Example 3

Photoswitching of a Spin-Transition Compound of the Family of the Iron(II) R-Triazole Compounds Inserted into a Spackling Filler Matrix (Plaster)

In this example, the reversible photoswitching of [Fe(NH$_2$-Trz)$_3$NO$_3$] was carried out after having inserted it, in a proportion of 5% by weight, in a spackling filler matrix (plaster) composed of 1 g of plaster powder per 10 ml of ethanol.

The same inscription system as that used above in example 2 was also used in this example. The diameter of the laser beam on the sample was 2 mm. The sweep rate was regulated at 1 cm·s$^{-1}$ and the power of the laser was regulated at 100 mW·cm$^{-2}$. Irradiation was carried out at a wavelength of 10.6 µm. Each letter was written by a single laser sweep, the beam being blocked before the inscription of each of the letters.

Figure 3:
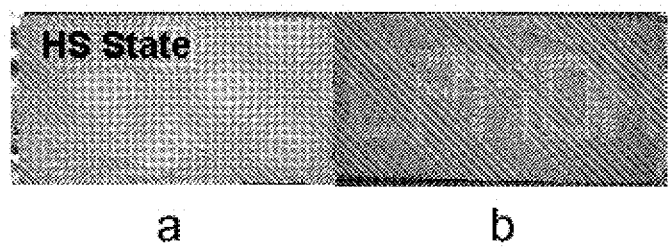
FIGS. 3(a)-3(b) are images of matrix incorporating the transition material of example, 3, in accordance with one embodiment.

The appended FIG. 3 is a photograph of the matrix incorporating the spin-transition material before irradiation (3a) and after irradiation (3b). In this case, the irradiation and the sweeping of the sample were carried out so as to obtain the script "CPMOH" at the surface of the matrix.

Example 4

Photoswitching of an "Irreversible" Spin-Transition Compound of the Family of the Iron(II) R-Triazole Compounds In this example, the photoswitching of the compound [Fe(R-Trz)$_3$X$_2$], with R=—(CH$_2$)$_2$OH and X=3-nitrophenylsulfonate, was carried out in the pure powder state or after its insertion into a polymer (PMMA) matrix or into a paint.

Incorporation in the Polymer Matrix:

the spin-transition compound was incorporated, in a proportion of 5% by weight, in the polymer matrix preprepared by dissolution of 1.2 g of PMMA in acetonitrile at 40° C. After deposition on a Plexiglas sheet and drying, a material was obtained consisting of a PMMA matrix in which the spin-transition compound was dispersed.

Incorporation in the Paint:

the spin-transition compound was incorporated, in a proportion of 10% by weight, in an alkyd lacquer paint. After deposition on a sheet, sold under the trade name Opacity Charts by Leneta, and drying, a material was obtained consisting of a paint in which the spin-transition compound was dispersed.

Each of the samples was illuminated by a laser beam with a diameter of 1 mm at a power of 150 mW·cm$^{-2}$. Irradiation was carried out at a wavelength of 10.6 µm.

Figure 4:
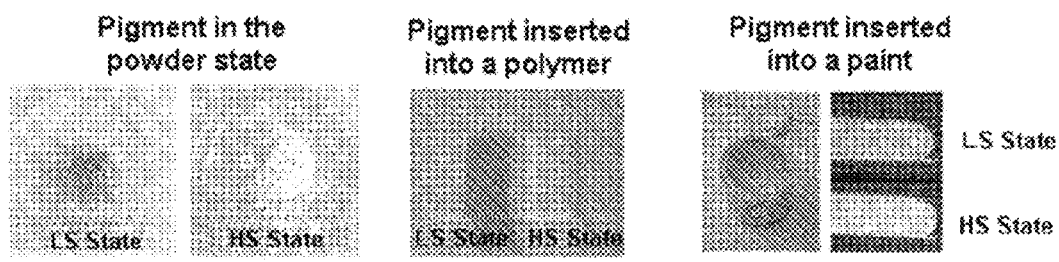
FIG. 4 is images of the material of example 4, in accordance with one embodiment.

The appended FIG. 4 shows photographs of each of the materials taken, before and after irradiation, on the crude material, that is to say on the spin-transition compound in the powder state (4a), on the material consisting of the PMMA matrix incorporating the spin-transition compound (4b) and on the material consisting of the paint incorporating the spin-transition material (4c).

Example 5

Photoswitching of an Irreversible Spin-Transition Compound of the Family of the Iron(II) R-Triazole Compounds Inserted into a Polymer Matrix In this example, the irreversible photoswitching was carried out of the compound [Fe(R-Trz)$_3$X$_2$], with R=—(CH$_2$)$_2$OH and X=3-nitrophenylsulfonate.

The compound studied was in the form of a powder formed of micrometric grains. The sample was illuminated by a laser beam having a diameter of approximately 1 mm and having a power of 150 mW·cm$^{-2}$. The sample was displaced, by hand, by the handler.

Figure 5:
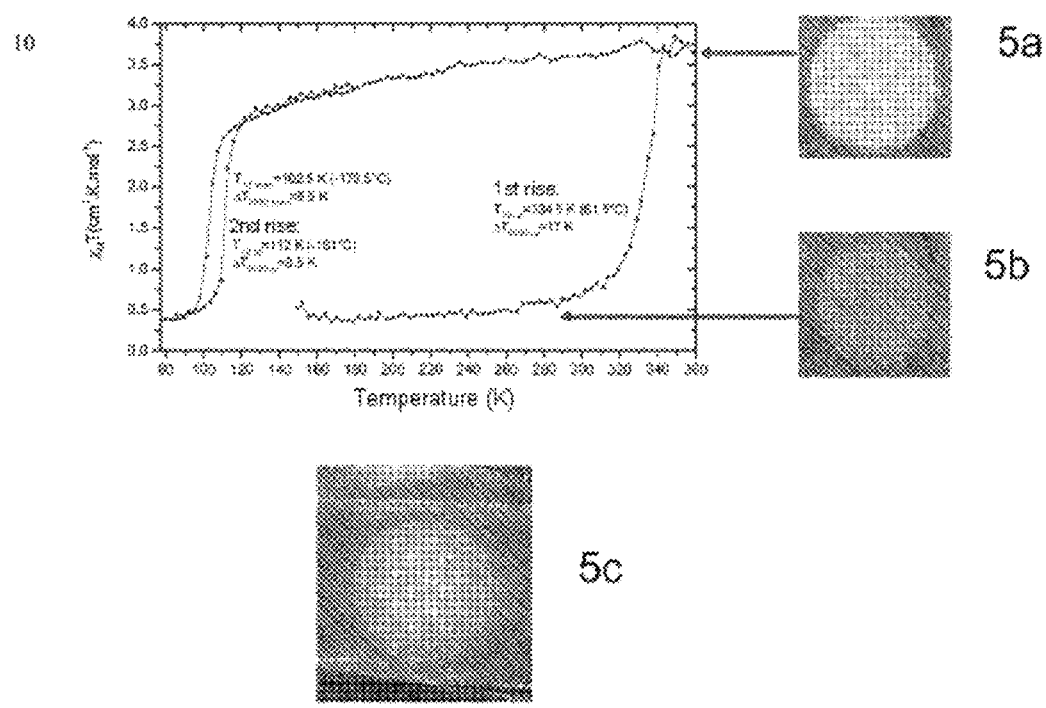
FIGS. 5(a)-5(c) are images of the material and a corresponding graph from exhibit 5, in accordance with one embodiment.

The appended FIG. 5 shows the change in the magnetic susceptibility and in the color of the powder as a function of the temperature of the sample.

A simple heat treatment process (process not forming part of the present invention) makes it possible for the powder, initially pink in the low spin state, to become white at high temperature. After a single heating cycle, the sample recovered its starting color (pink) only at very low temperature (T<100 K). The change in the spin state of the compound was confirmed by the magnetic susceptibility measurements presented.

This same compound, not having been subjected to any preliminary heat treatment (LS state—FIG. 5b), was exposed to a laser beam according to the process in accordance with the present invention. The power and the wavelength of the radiation were 150 mW·cm$^{-2}$ and 10.6 µm respectively. The illuminated region became white (FIG. 5a). The temperature of the sample was then lowered below 100 K and the whole of the sample became pink. The part which had been exposed to the laser radiation resumed its white color as soon as the temperature of the sample was brought above 130 K and the regions illuminated and not illuminated by the laser beam appear clearly (FIG. 5c). Finally, the sample was heated above 360 K and the whole of the compound then became white. The temperature behavior of the compound is then similar to that of a heated sample.

The invention claimed is:

1. A process for the photoswitching of a spin-transition material from the low spin state to the high spin state, said spin-transition material having a compound based on iron(II) and on a triazole ligand, said method comprising the step of:
   at least one stage of exposure of said material to unpolarized laser radiation at a wavelength varying from 0.78 to 30 µm, within the infrared range, at ambient temperature and at a power of from 1 mW·cm$^{-2}$ to 1 W·cm$^{-2}$.

2. The process as claimed in claim 1, wherein the spin-transition material is subjected to continuous laser radiation.

3. The process as claimed in claim 1, wherein the power of the laser radiation varies from 80 to 500 mW·cm$^{-2}$.

4. The process as claimed in claim 1, wherein the duration of the exposure of the spin-transition material to the laser radiation varies from a few milliseconds at a power of 100 mW·cm$^{-2}$ to approximately a hundred seconds at a power of 1 mW·cm$^{-2}$.

5. The process as claimed in claim 1, wherein the size of the laser beam varies from 100 µm in diameter at a power of 100 mW·cm$^{-2}$ to 1 mm at a power of 1 W·cm$^{-2}$.

6. The process as claimed in claim 1, wherein the spin-transition material is in the form of particles or is incorporated in dispersed form in a solid matrix.

7. The process as claimed in claim 6, wherein the solid matrix is selected from the group consisting of plaster, varnishes, cements, paints and polymer matrices.

8. The process as claimed in claim 1, wherein the spin-transition material is chosen from nanometric particles essentially comprising a compound corresponding to the following formula (I):

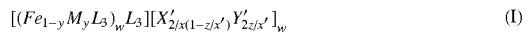

$$[(Fe_{1-y}M_yL_3)_wL_3][X'_{2/x(1-z/x')}Y'_{2z/x'}]_w \qquad (I)$$

in which:
  L represents a 1,2,4-triazole ligand carrying an R substituent on the nitrogen in the 4 position;
  X' is an anion having the valency x, $1 \leq x \leq 2$;
  Y' is an anion other than X having the valency x', $1 \leq x' \leq 2$;
  R is an alkyl group or an $R^1R^2N$— group in which $R^1$ and $R^2$ each represent, independently of the other, H or an alkyl radical;
  M is a metal having a $3d^4$, $3d^5$, $3d^6$ or $3d^7$ configuration, other than Fe;
  $0 \leq y \leq 1$, $0 \leq z \leq 2$ and $3 \leq w \leq 1500$.

9. The process as claimed in claim 1, wherein the spin-transition material is chosen from materials composed of at least one compound corresponding to the following formula (II):

$$AX_bY_c \qquad (II)$$

in which:
  A corresponds to the formula $Fe_{1-m}M_m(R\text{-}Trz)_3$;
  M is a metal having a $3d^4$, $3d^5$, $3d^6$ or $3d^7$ configuration, other than Fe;
  $0 \leq m \leq 1$;
  R-Trz represents a 1,2,4-triazole ligand carrying an R substituent on the nitrogen in the 4 position;
  R is an alkyl group or a group $R^1R^2N$— in which $R^1$ and $R^2$ each represent, independently of the other, H or an alkyl radical;
  X represents at least one monovalent or divalent anion;
  Y represents at least one anion which has a chromophore group;
  b and c are chosen so that the electrical neutrality of the compound (II) is respected.

10. The process as claimed in claim 9, wherein Y is chosen from chromophoric anions which have at least two aromatic rings and at least one $SO_3^-$ group.

11. The process as claimed in claim 9, wherein the spin-transition material is a material for which the spin transition from the high spin state to the low spin state is irreversible at ambient temperature and which is chosen from the compounds of formula (II) in which the R substituent of the 1,2,4-triazole ligand is a hydroxyalkyl radical and X is a 3-nitrophenylsulfonate anion.

12. The method as claimed in claim 1, further comprising the step of marking materials comprising particles of at least one spin-transition compound comprising a compound based on iron(II) and on a triazole ligand.

13. The method as claimed in claim 1, further comprising the step of any one of processing information, storing data and optical addressing.

* * * * *